United States Patent
Spinelli et al.

(10) Patent No.: US 8,219,197 B2
(45) Date of Patent: *Jul. 10, 2012

(54) APPARATUS AND METHOD FOR TESTING AND ADJUSTING A BIPOLAR STIMULATION CONFIGURATION

(75) Inventors: Julio C. Spinelli, Buenos Aires (AR); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/852,875

(22) Filed: Aug. 9, 2010

(65) Prior Publication Data

US 2010/0305644 A1 Dec. 2, 2010

Related U.S. Application Data

(63) Continuation of application No. 11/836,502, filed on Aug. 9, 2007, now Pat. No. 7,774,065, which is a continuation of application No. 11/153,999, filed on Jun. 16, 2005, now Pat. No. 7,257,444, which is a continuation of application No. 10/634,202, filed on Aug. 5, 2003, now Pat. No. 6,915,163, which is a continuation of application No. 09/748,765, filed on Dec. 26, 2000, now Pat. No. 6,611,712.

(51) Int. Cl.
*A61N 1/362* (2006.01)
(52) U.S. Cl. ................ 607/28; 607/9; 607/11
(58) Field of Classification Search ........ 607/9, 11, 607/27, 28, 122
See application file for complete search history.

(56) References Cited

U.S. PATENT DOCUMENTS

| | | | |
|---|---|---|---|
| 4,686,988 A * | 8/1987 | Sholder | 607/28 |
| 5,222,493 A * | 6/1993 | Sholder | 607/27 |
| 5,324,310 A | 6/1994 | Greeninger et al. | |
| 5,480,414 A | 1/1996 | Stroebel et al. | |
| 5,601,615 A | 2/1997 | Markowitz et al. | |
| 5,674,254 A | 10/1997 | van Krieken | |
| 5,713,933 A | 2/1998 | Condie et al. | |
| 5,718,720 A | 2/1998 | Prutchi et al. | |
| 5,741,312 A | 4/1998 | Vonk et al. | |
| 5,766,230 A | 6/1998 | Routh et al. | |
| 5,843,137 A | 12/1998 | Condie et al. | |
| 5,855,594 A | 1/1999 | Olive et al. | |
| 5,861,013 A | 1/1999 | Peck et al. | |
| 5,871,512 A | 2/1999 | Hemming et al. | |
| 5,902,325 A | 5/1999 | Condie et al. | |
| 6,611,712 B2 | 8/2003 | Spinelli et al. | |
| 6,915,163 B2 | 7/2005 | Spinelli et al. | |

(Continued)

OTHER PUBLICATIONS

"U.S. Appl. No. 11/836,502, Non Final Office Action Mailed Sep. 17, 2009", 6 pgs.

(Continued)

*Primary Examiner* — Carl H Layno
*Assistant Examiner* — Pamela M Bays
(74) *Attorney, Agent, or Firm* — Schwegman, Lundberg & Woessner, P.A.

(57) ABSTRACT

A system and method for measuring the capture threshold of a bipolar lead in order to determine an appropriate value for the stimulus pulse energy to be used with the lead by a cardiac rhythm management device. An appropriate bipolar stimulating configuration can also be determined. The method is particularly useful in testing bipolar leads used to excite the left ventricle such as when delivering cardiac resynchronization therapy.

20 Claims, 3 Drawing Sheets

U.S. PATENT DOCUMENTS

| | | |
|---|---|---|
| 7,257,444 B2 | 8/2007 | Spinelli et al. |
| 2005/0234520 A1 | 10/2005 | Spinelli et al. |
| 2007/0276446 A1 | 11/2007 | Spinelli et al. |

OTHER PUBLICATIONS

"U.S. Appl. No. 09/748,765, Non-final office action mailed Jun. 28, 2002", 6 pgs.

"U.S. Appl. No. 09/748,765, Notice of allowance mailed Jan. 7, 2003", 4 pgs.

"U.S. Appl. No. 09/748,765, Response filed Oct. 28, 2002 to Non-final office action mailed Jun. 28, 2002", 5 pgs.

"U.S. Appl. No. 10/634,202, Non final Office Action mailed Sep. 3, 2004", 9 pgs.

"U.S. Appl. No. 10/634,202, Notice of Allowance mailed Feb. 25, 2005", 6 pgs.

"U.S. Appl. No. 10/634,202, Response filed Dec. 6, 2004 to Non Final Office Action mailed Sep. 3, 2004", 8 pgs.

"U.S. Appl. No. 11/153,999, Non Final Office Action mailed Oct. 6, 2006", 9 pgs.

"U.S. Appl. No. 11/153,999, Notice of Allowance mailed Apr. 6, 2007", 4 pgs.

"U.S. Appl. No. 11/153,999, Response filed Jan. 8, 2007 to Non Final Office Action mailed Oct. 6, 2006", 8 pgs.

"U.S. Appl. No. 11/836,502, Notice of Allowance mailed Apr. 6, 2010", 7 pgs.

"U.S. Appl. No. 11/836,502, Response filed Dec. 17, 2009 to Non Final Office Action mailed Sep. 17, 2009", 8 pgs.

* cited by examiner

APPARATUS AND METHOD FOR TESTING AND ADJUSTING A BIPOLAR STIMULATION CONFIGURATION

CLAIM OF PRIORITY

This application is a continuation of and claims the benefit of priority under 35 U.S.C. §120 to U.S. patent application Ser. No. 11/836,502, filed on Aug. 9, 2007, now issued as U.S. Pat. No. 7,774,065, which is a continuation of and claims the benefit of priority under 35 U.S.C. §120 to U.S. patent application Ser. No. 11/153,999, filed Jun. 16, 2005, now issued as U.S. Pat. No. 7,257,444, which is a continuation of and claims the benefit of priority under 35 U.S.C. §120 to U.S. patent application Ser. No. 10/634,202, filed Aug. 5, 2003, now issued as U.S. Pat. No. 6,915,163, which is a continuation of and claims the benefit of priority under 35 U.S.C. §120 to U.S. patent application Ser. No. 09/748,765, filed on Dec. 26, 2000, now issued as U.S. Pat. No. 6,611,712, the specifications of which are incorporated herein by reference.

FIELD OF THE INVENTION

This invention pertains to cardiac rhythm management devices and, in particular, to systems and methods for testing such devices in order to appropriately set operating parameters.

BACKGROUND

Cardiac rhythm management devices are devices that either pace or otherwise excite selected chambers of the heart by electrical stimulation. A pacemaker, for example, is a cardiac rhythm management device that enforces a particular heart rate by delivering pacing pulses to the heart in response to lapsed time intervals and sensed cardiac electrical activity (i.e., intrinsic heart beats). Cardiac rhythm management devices, either in addition to or instead of pacing the heart, may also deliver stimulation pulses in order to excite a particular chamber or region of a chamber in synchrony with sensed intrinsic cardiac activity occurring elsewhere. Such devices are typically implanted subcutaneously on a patient's chest and have leads threaded intravenously into the heart to connect the device to the electrodes used for sensing and stimulation.

In order to cause a contraction in the absence of intrinsic activity (referred to herein as excitation), the stimulus pulses delivered to the heart by the device must achieve "capture," which refers to causing sufficient depolarization of the myocardium that a propagating wave of excitation and contraction result (i.e., a heart beat). A stimulus pulse that does not capture the heart is thus an ineffective pulse. This not only wastes energy from the battery of the device, but can have deleterious physiological effects as well. For example, a pacemaker that is not achieving capture is not performing its function in enforcing a minimum heart rate. For a particular implanted lead, a capture threshold exists which is the lowest energy pulse that will achieve capture when a stimulus pulse is output through the lead. (The energy of a stimulus pulse is determined by the voltage and duration of the pulse.) A common technique used to determine if capture is present during a given cardiac cycle is to look for an "evoked response" immediately following a stimulus pulse. The evoked response is the wave of depolarization that results from the stimulus pulse and evidences that the stimulated chamber has responded appropriately and contracted. In the case of ventricular stimulation, by detecting the evoked R-wave, the device is able to detect whether the stimulus pulse was effective in capturing the heart, that is, causing a ventricular contraction. Capture verification can be performed by a clinician using an external programmer to adjust operating parameters and monitor sensing data to ensure that the heart is reliably paced and/or otherwise excited. Alternatively, a cardiac rhythm management device may be programmed to perform capture verification tests automatically, either at periodic intervals or upon a command from an external programmer.

Stimulation/sensing leads are generally of two types, bipolar and unipolar. A unipolar lead has one electrode at its distal end connected to a conductor within the lead which is covered by insulation. A bipolar lead has two conductors which are respectively connected to a distal and proximal electrode. The distal electrode is usually a tip electrode which may be fixed into the myocardium, and the proximal electrode is a ring electrode around the body of the lead. In bipolar stimulation, a stimulus pulse is output between two electrodes, and in bipolar sensing, the voltage difference between the two electrodes is sensed. A bipolar stimulus pulse may be output with a polarity such that one electrode is the cathode (electrically negative) and the other electrode is the anode (electrically positive). In unipolar sensing/stimulation, the electrode at the end of the lead is used as either a cathode or anode, and the housing of the device or an electrode on another lead is used as an electrode of the opposite polarity, referred to as a reference. Cathodal stimulation of the myocardium is generally preferred because it has a lower and more stable capture threshold. Cardiac rhythm management devices with bipolar leads may typically be programmed to deliver either bipolar or unipolar stimulus pulses through a lead. Bipolar stimulation is preferred by some clinicians, however, because it more precisely delivers energy to the heart with less risk of causing contractions of overlying skin or skeletal muscle.

Once a cardiac rhythm management device has been implanted, a clinician typically sets up the configuration of the device using an external programmer. Among the parameters that can be adjusted during this process, is the stimulus pulse energy for a given lead, which is normally set to a value corresponding to the capture threshold determined for that lead. For example, the stimulus pulse energy may be set to the value of the capture threshold plus some specified safety margin. The present invention is directed toward an improved method and apparatus for adjusting the stimulation parameters of a cardiac rhythm management device employing bipolar stimulation.

SUMMARY OF THE INVENTION

The present invention is an apparatus and method for testing the capture threshold of a bipolar lead of a cardiac rhythm management device in order to determine an appropriate stimulus pulse energy for the lead and/or select an appropriate stimulation configuration. The method is particularly useful with bipolar leads used to excite the left ventricle such as when delivering cardiac resynchronization therapy.

In one embodiment, a unipolar capture threshold is measured for the cathode of a bipolar lead, and the bipolar stimulus pulse energy is set to correspond to the measured unipolar cathodal threshold. Alternatively, the bipolar capture threshold using the anode and cathode of the lead is also measured, and the bipolar stimulus pulse energy is then set to the greater of the measured bipolar capture threshold and the measured unipolar cathodal capture threshold.

In another embodiment of the invention, a stimulation configuration is determined for a bipolar lead having proximal and distal electrodes. Unipolar capture thresholds for the proximal and distal electrodes of a bipolar lead are measured, and the electrode of the bipolar lead having the lowest unipolar capture threshold is selected as the cathode for bipolar stimulation, with the other electrode serving as the anode. The stimulus pulse energy for bipolar stimulation may then be set to correspond to the measured unipolar capture threshold for the electrode selected to be the cathode. Alternatively, the bipolar capture threshold for the configuration is also measured, and the bipolar stimulus pulse energy is set to the greater of the measured bipolar capture threshold and the measured unipolar cathodal capture threshold.

DETAILED DESCRIPTION OF THE INVENTION

Figure 1:
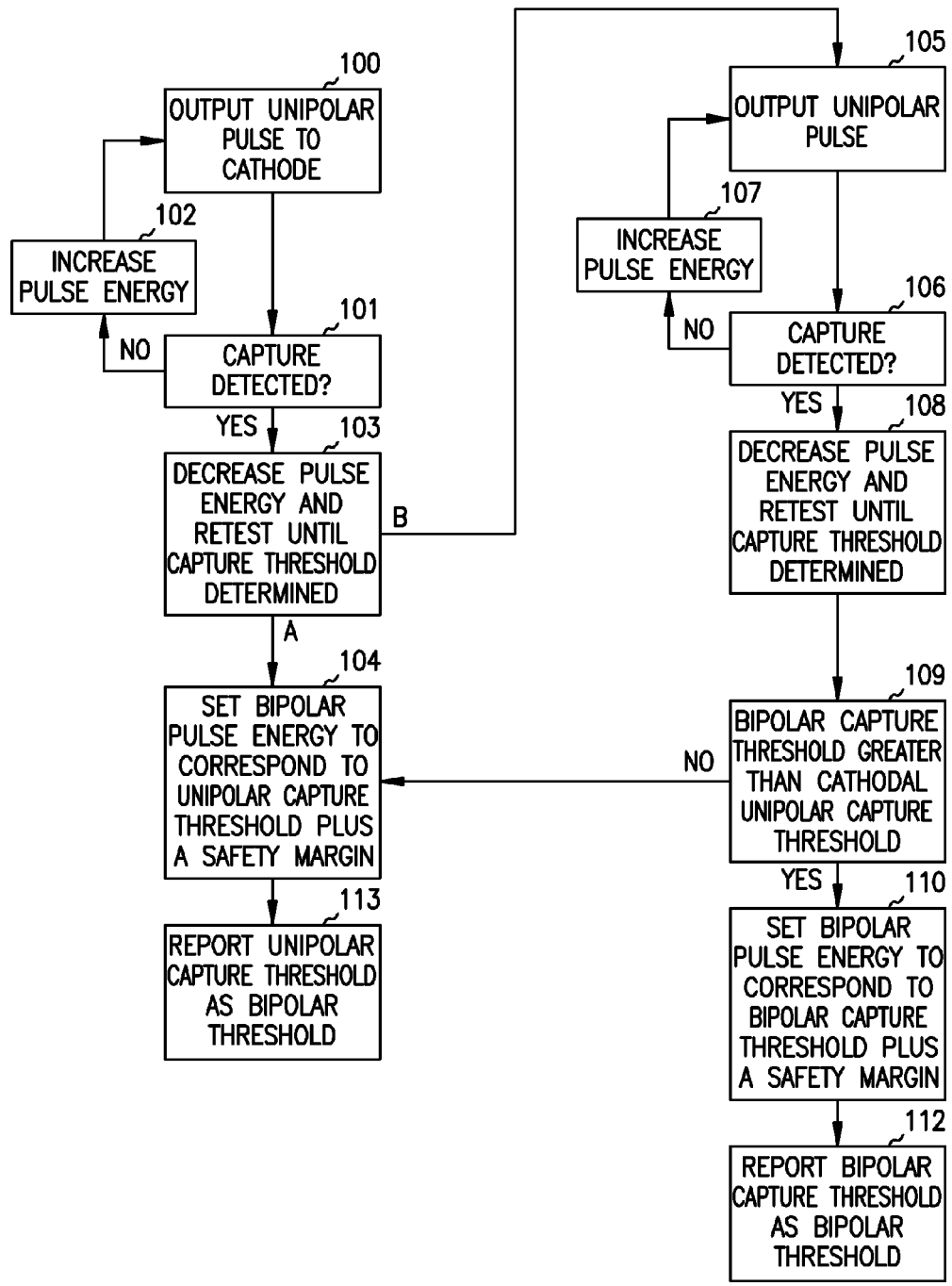
FIGS. 1 and 2 illustrate particular embodiments of a method for adjusting stimulation parameters.

Pacing therapy has been found to be useful in treating congestive heart failure (CHF), a clinical syndrome in which an abnormality of cardiac function causes cardiac output to fall below a level adequate to meet the metabolic demand of peripheral tissues. It has also been shown that some CHF patients suffer from intraventricular conduction defects (a.k.a. bundle branch blocks). The cardiac outputs of these patients can be increased by improving the synchronization of right and left ventricular contractions with biventricular pacing or left ventricular pacing/excitation, or by improving the synchrony of contractions of the septum and free wall of a ventricle, both of which are referred to as cardiac resynchronization therapy.

In order to excite the left ventricle, the lead must be disposed near the left ventricle, preferably in the region of the free lateral or posterior wall, which may most easily be accomplished by placing the lead through the coronary sinus and into a left cardiac vein. Unlike a lead for the right ventricle, which is disposed within the ventricle where a tip electrode can be fixed into the myocardium, the electrodes of a lead in a cardiac vein cannot be fixed into the myocardium since that would require puncturing the vein. Instead, in the case of a bipolar lead, both the tip and ring electrodes (or proximal and distal electrodes in the case where both electrodes are ring electrodes or other types of structures) are positioned within the vein adjacent to the left ventricular myocardium.

Because it is fixed into the myocardium, the tip of a bipolar lead in the right ventricle has a lower capture threshold than the ring electrode. Normally, therefore, the tip of a bipolar lead is used as the cathode in order to achieve the desirable cathodal capture when a voltage pulse is impressed across the two electrodes. (Cathodal capture means that cathodal stimulation is responsible for the contraction.) With a bipolar lead in a cardiac vein, on the other hand, both electrodes are external to the myocardium and may have similar capture thresholds so that either anodal or cathodal capture can occur when a pacing pulse is output through the lead. It has been found, however, that anodal thresholds increase over time so that eventually only the desired cathodal capture will occur. Nevertheless, a problem arises when the pulse energy for a bipolar lead in a cardiac vein is adjusted. When the lead is implanted, the capture threshold for the tip or distal electrode (i.e., the electrode usually selected to function as the cathode) may be higher than that of the ring or proximal electrode. When the clinician then determines the capture threshold of the lead with a bipolar pulse in order to adjust the stimulus pulse energy, it is impossible to distinguish between anodal and cathodal capture. There is then a risk that the stimulus pulse energy will be set to an anodal capture threshold when the cathodal capture threshold is higher. As the anodal capture threshold increases over time, the stimulus pulses may no longer be of sufficient energy to excite the left ventricle (diminishing or eliminating the programmed safety margin), and the patient may experience sporadic or total loss of resynchronization therapy.

As aforesaid, if the capture threshold of a bipolar lead is measured, it may be impossible to tell whether it is anodal or cathodal capture that is being measured. This problem may be overcome by measuring a unipolar capture threshold for the electrode of the lead that is to be used as a cathode. The stimulus pulse energy for bipolar stimulation is then set to correspond to the measured unipolar cathodal threshold, either manually or automatically. That is, the bipolar stimulus pulse energy is set equal to the unipolar cathodal threshold plus a specified safety margin. In the case where the stimulus pulse energy is manually adjusted, the bipolar threshold is reported to the clinician as the unipolar measurement with the cathodal lead, and the clinician then adjusts the bipolar stimulus energy accordingly with a specified safety margin. This avoids the problem of using a measured bipolar capture threshold and inadvertently setting the bipolar stimulus energy to correspond with an anodal capture threshold. Alternatively, the bipolar capture threshold is also measured, and the bipolar stimulus pulse energy is set to correspond to the greater of the bipolar and unipolar cathodal capture thresholds. In the case where the stimulus pulse energy is manually adjusted, the bipolar threshold is reported to the clinician using the larger of the bipolar and unipolar measurements. FIG. 1 illustrates the steps involved in performing a particular implementation of the method. At steps 100 through 103, unipolar pulses are output to the cathode to determine the minimum pulse energy that results in capture. Various algorithms may be used to accomplish this, but all involve increasing and decreasing the pulse energy while testing for capture until the capture threshold is determined. After the unipolar cathodal capture threshold is determined at step 103, two alternative means for determining the bipolar pulse energy are shown in FIG. 1, designated A and B. In alternative A, the bipolar pulse energy is set to correspond to the measured unipolar threshold at step 104. In alternative B, a bipolar capture threshold is determined at steps 105 through 108, and the unipolar and bipolar thresholds are compared at step 109. If the bipolar capture threshold is greater than the unipolar capture threshold, the bipolar pulse energy is set to correspond to the bipolar capture threshold (with a specified safety margin) at step 110 and/or the bipolar capture threshold is reported as the measured bipolar capture threshold at step 112. Otherwise, the bipolar pulse energy is set to correspond to the unipolar capture threshold (with a specified safety margin) at step 104 and/or the bipolar capture threshold is reported as the measured unipolar capture threshold at step 113.

Figure 2:
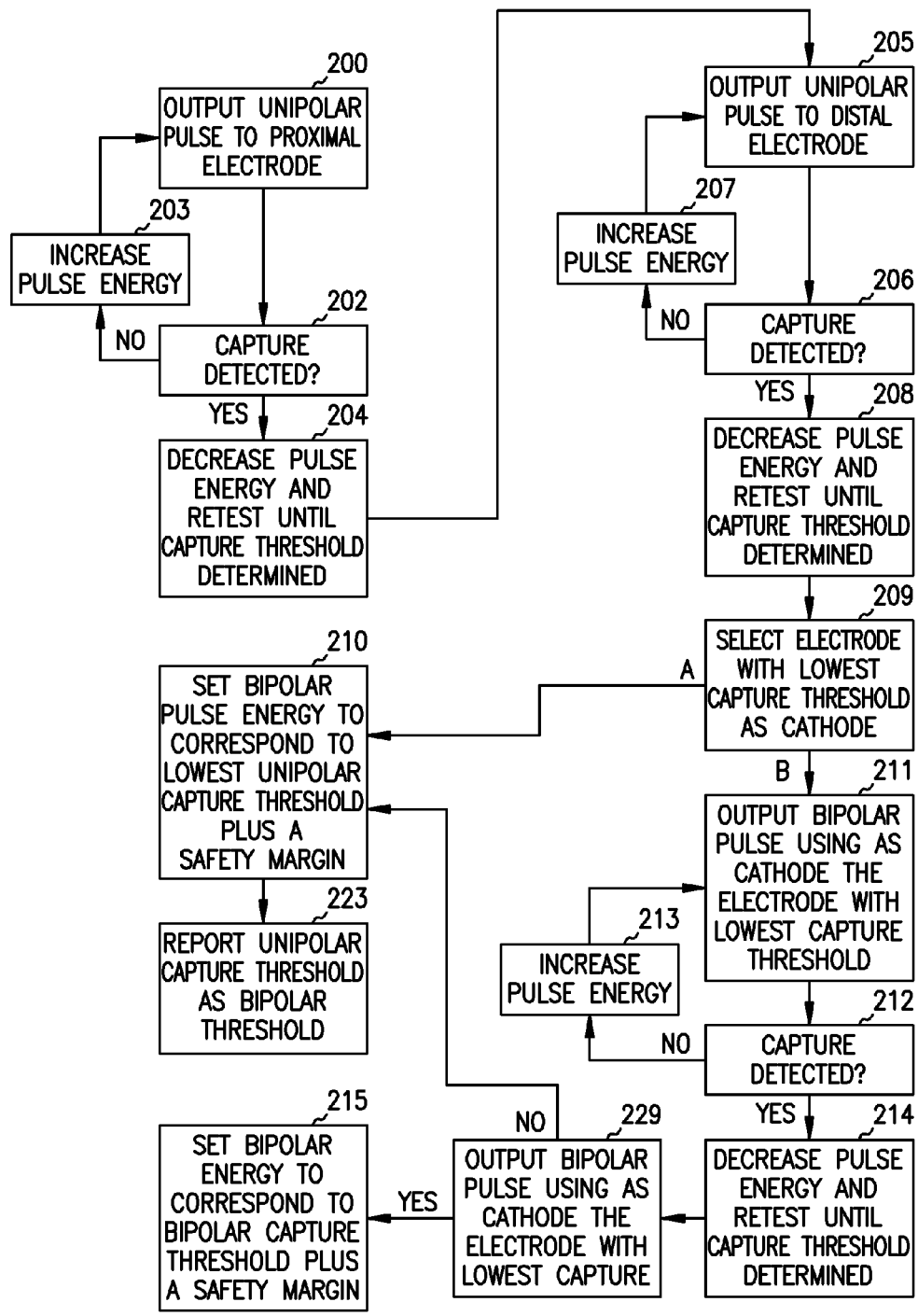

In another embodiment, a bipolar stimulation configuration is determined by measuring the unipolar capture thresholds for both electrodes of a bipolar lead and selecting the electrode with the lower threshold as the cathode for bipolar pacing. The bipolar stimulus pulse energy is then set to correspond to the determined lower unipolar capture threshold. Alternatively, the bipolar capture threshold is also measured, and the bipolar stimulus pulse energy is set to correspond to the greater of the bipolar and unipolar cathodal capture thresholds. FIG. 2 illustrates the steps of an exemplary implementation of this method. At steps 200 through 204, the unipolar capture threshold for the proximal electrode is determined, and the unipolar capture threshold for the distal electrode is determined at steps 205 through 208. At step 209, the electrode with the lowest unipolar capture threshold is selected as the cathode for bipolar stimulation. Two alternatives are shown for setting the bipolar stimulus pulse energy. In alternative A, the bipolar stimulus pulse energy is set to correspond to the lowest unipolar capture threshold at step 210, and/or the bipolar capture threshold is reported as the measured unipolar capture threshold at step 223. In alternative B, a bipolar capture threshold is determined at steps 211 through 214, and the unipolar and bipolar thresholds are compared at step 229. If the bipolar capture threshold is greater than the cathodal unipolar capture threshold, the bipolar pulse energy is set to correspond to the measured bipolar capture threshold at step 215. Otherwise, the bipolar pulse energy is set to correspond to the lowest measured unipolar capture threshold at step 210 and/or the bipolar capture threshold is reported as the measured lowest unipolar capture threshold at step 223.

Figure 3:
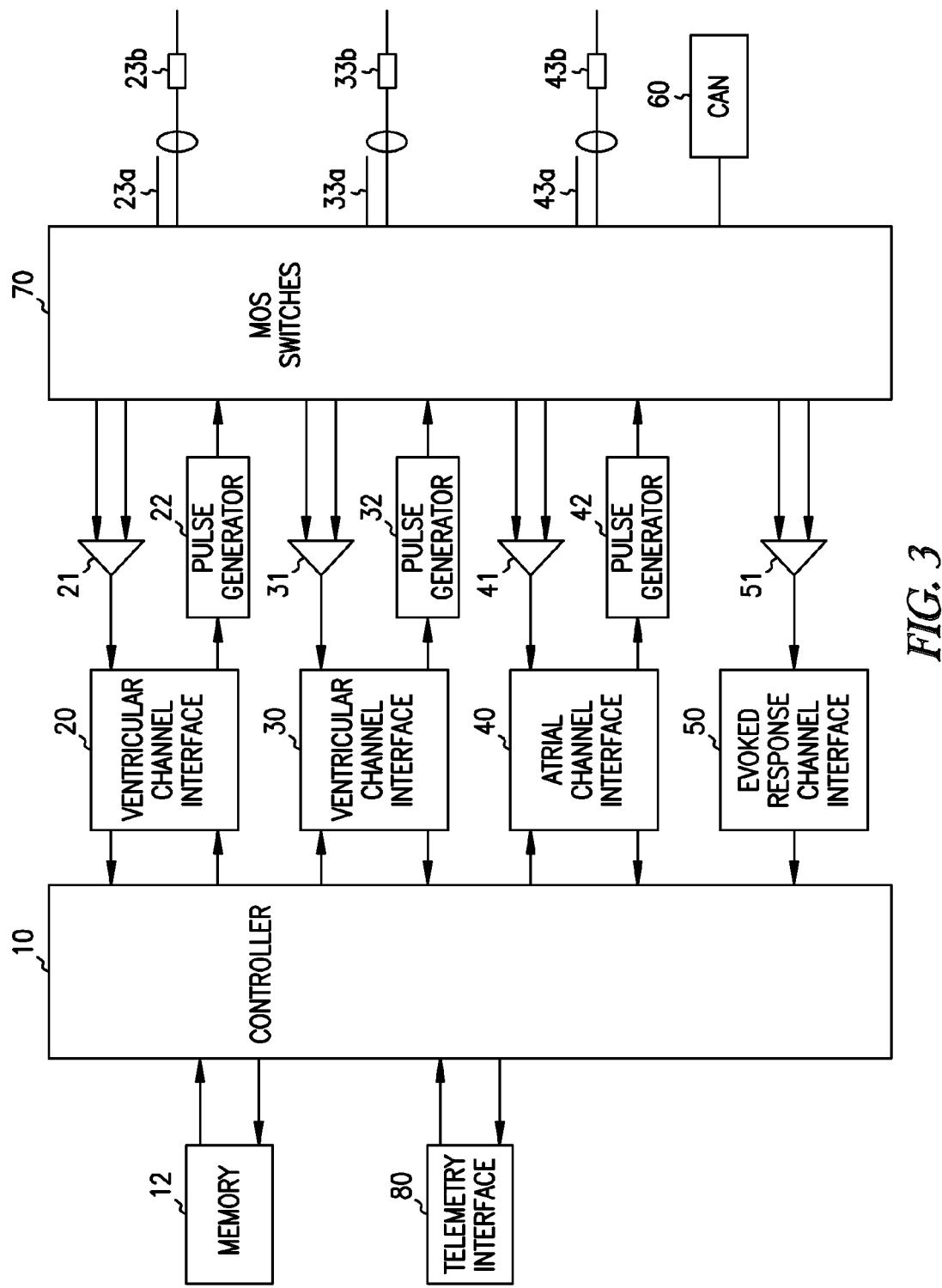
FIG. 3 is a block diagram of a cardiac rhythm management device.

A block diagram of a cardiac rhythm management device having an atrial and two ventricular sensing/stimulation channels is shown in FIG. 3. The control unit of the device is made up of a microprocessor 10 communicating with a memory 12 via a bidirectional data bus 13, where the memory 12 typically comprises a ROM (read-only memory) for program storage and a RAM (random-access memory) for data storage. The control unit could be implemented by other types of logic circuitry (e.g., discrete components or programmable logic arrays) using a state machine type of design, but a microprocessor-based system is preferable. The control unit is capable of operating the device in a number of programmed pacing and/or resynchronization modes which defines how stimulation pulses are output in response to sensed events and expiration of time intervals. A telemetry interface 80 is also provided for communicating with an external programmer.

The device has an atrial sensing/stimulation channel comprising a bipolar lead made up of ring electrode 43a and tip electrode 43b, sense amplifier 41, pulse generator 42, and an atrial channel interface 40 which communicates bidirectionally with a port of microprocessor 10. The device also has two ventricular sensing/stimulation channels that similarly include a bipolar lead made up of ring (or proximal) electrode 23a and tip (or distal) electrode 23b, a bipolar lead made up of ring (or proximal) electrode 33a and tip (or distal) electrode 33b, sense amplifiers 21 and 31, pulse generators 22 and 32, and ventricular channel interfaces 20 and 30. For each channel, the same lead and electrode are used for both sensing and stimulation. The device also has an evoked response sensing channel that comprises an evoked response channel interface 50 and a sense amplifier 51. The evoked response sensing channel enables the controller to determine if capture has been achieved by a stimulus pulse by sensing whether or not an evoked potential occurs subsequent to the pulse. The channel interfaces include analog-to-digital converters for digitizing sensing signal inputs from the sensing amplifiers, registers that can be written to for adjusting the gain and threshold values of the sensing amplifiers, and, in the case of the ventricular and atrial stimulation channel interfaces, registers for controlling the output of stimulus pulses and/or changing the stimulus pulse voltage amplitude.

Still referring to FIG. 3, the electrodes are connected to the sense amplifiers and pulse generators by means of a switching circuit 70 which enables the amplifiers and pulse generators to be connected to selected tip or ring electrodes of any of the sensing/stimulation channels that connect through the switching circuit 70, as well as to the device housing or can 60, which is also electrically connected to the switching circuit. The configuration of the switching circuit 70 is preferably implemented as an array of MOSFET transistors controlled by outputs of the controller 10. Switching circuit 70 enables any of the tip or ring electrodes of the sensing channels or the device housing to be used as a cathode or anode.

The capture threshold for a stimulation channel is determined by testing the channel using the dedicated evoked response sensing channel. In this test, it is determined whether or not a sensing/pacing channel is achieving capture with the stimulus pulses delivered by the channel's lead. The evoked response sensing channel includes a sense amplifier for sensing an evoked response generated after a stimulus pulse is delivered. The evoked response sensing channel is connected to a selected electrode of the pacemaker's sensing/stimulation channels by means of the switching circuit 70. After switching the input of the evoked response sensing channel to the electrode that is to be tested to verify capture, a stimulation pulse is output and an evoked response is either detected or not, signifying the presence or loss of capture, respectively.

A cardiac rhythm management device with a bipolar pacing lead such as illustrated in FIG. 3 may be programmed to perform any of the methods described above with reference to FIGS. 1 and 2 in order to determine a bipolar stimulus pulse energy and/or a bipolar stimulation configuration for the device. The programming may specify that the method steps are performed either upon request from a clinician via an external programmer or automatically at periodic intervals. In the former case, the device may either automatically set the parameters to the appropriate values as determined by the device or may report an appropriate stimulation configuration and/or bipolar stimulus energy via the external programmer, with those parameters either being selected or not for configuring the device by the clinician.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   a controller for controlling the operation of the device;
   a sense amplifier for receiving sense signals;
   a pulse generator for outputting stimulus pulses;
   a switching circuit interfaced to the controller for connecting the sense amplifier and pulse generator to selected electrodes of a lead having first and second electrodes and for connecting the sense amplifier to a third electrode;
   wherein the controller is programmed to output stimulus pulses to the selected electrodes at selected pulse energies from the pulse generator and to determine a capture threshold by detecting evoked responses with the sense amplifier; and,
   wherein the controller is programmed to measure unipolar capture thresholds for each of the first and second electrodes of the lead using the third electrode as a reference and determine which of the first and second electrodes has the lower unipolar capture threshold.

2. The device of claim 1 wherein the controller is further programmed to automatically operate the switching circuit in order to select the electrode of the lead having the lower unipolar capture threshold as a cathode for bipolar stimulation and the other electrode of the lead as an anode.

3. The device of claim 1 wherein the controller is programmed to measure unipolar capture thresholds for each of the first and second electrodes of the lead using a third electrode as a reference and determine which of the first and second electrodes has the lower unipolar capture threshold automatically at periodic intervals.

4. The device of claim 1 further comprising a telemetry interface for communicating with an external programmer and wherein the controller is programmed to report to the external programmer an appropriate bipolar stimulation configuration specifying the electrode of the lead having the lower unipolar capture threshold as a cathode and the other electrode of the lead as an anode.

5. The device of claim 4 wherein the controller is programmed to measure unipolar capture thresholds for each of the first and second electrodes of the lead using a third electrode as a reference and determine which of the first and second electrodes has the lower unipolar capture threshold when requested by the external programmer.

6. The device of claim 1 wherein the switching circuit is operated in order to select the electrode of the lead having the lower unipolar capture threshold as a cathode for bipolar stimulation and the other electrode of the lead as an anode and wherein the controller is further programmed to determine a stimulus pulse energy for bipolar stimulation as a value corresponding to the measured unipolar capture threshold for the electrode selected to be the cathode.

7. The device of claim 6 further comprising a telemetry interface for communicating with an external programmer and wherein the controller is programmed to report to the external programmer the determined stimulus pulse energy for bipolar stimulation.

8. The device of claim 6 wherein the controller is programmed to automatically set the stimulus pulse energy for bipolar stimulation.

9. The device of claim 1 wherein the switching circuit is operated in order to select the electrode of the lead having the lower unipolar capture threshold as a cathode for bipolar stimulation and the other electrode of the lead as an anode and wherein the controller is further programmed to measure a bipolar capture threshold and to determine a stimulus pulse energy for bipolar stimulation as a value corresponding to the greater of either the measured bipolar capture threshold or the measured unipolar capture threshold for the electrode selected to be the cathode.

10. The device of claim 9 further comprising a telemetry interface for communicating with an external programmer and wherein the controller is programmed to report to the external programmer the determined stimulus pulse energy for bipolar stimulation.

11. The device of claim 9 wherein the controller is programmed to automatically set the stimulus pulse energy for bipolar stimulation.

12. The device of claim 1 wherein the third electrode for unipolar capture threshold measurement is a housing of the device.

13. The device of claim 1 wherein the third electrode for unipolar capture threshold measurement is another electrode incorporated into a lead.

14. A device for delivering stimulation pulses to the heart, comprising:
   means for delivering stimulation pulses to first and second electrodes of a lead in a bipolar stimulation configuration, to the first electrode of the lead in a unipolar stimulation configuration, or to the second electrode of the lead in a unipolar stimulation configuration;
   means for measuring capture thresholds of the unipolar stimulation configurations using the first and second electrodes;
   means for selecting a bipolar stimulation configuration as one in which the cathode is whichever of the first and second electrodes has the lower unipolar capture threshold.

15. The device of claim 14 wherein the means for selecting a bipolar stimulation configuration includes a device controller programmed to automatically make the selection.

16. The device of claim 14 wherein the means for selecting a bipolar stimulation configuration includes an external programmer communicating with a device controller via telemetry.

17. The device of claim 14 further comprising means for determining a stimulus pulse energy for bipolar stimulation as a value corresponding to the measured unipolar capture threshold for the electrode selected to be the cathode.

18. The device of claim 17 further comprising means for setting the stimulus pulse energy for bipolar stimulation.

19. The device of claim 14 further comprising means for determining a stimulus pulse energy for bipolar stimulation as a value corresponding to the greater of either the measured bipolar capture threshold or the measured unipolar capture threshold for the electrode selected to be the cathode.

20. The device of claim 19 further comprising means for setting the stimulus pulse energy for bipolar stimulation.

* * * * *